(12) United States Patent
Esser et al.

(10) Patent No.: US 11,596,458 B2
(45) Date of Patent: *Mar. 7, 2023

(54) IMPLANT FOR BONE FIXATION (71) Applicant: Stryker European Operations Holdings LLC, Kalamazoo, MI (US)

(72) Inventors: Matthias Esser, Freiburg (DE); Gheorghe Marton, Freiburg (DE); Eva Beutel, Freiburg (DE); Christian Knoepfle, Donaueschingen (DE); Manfred Schmuck, Muehlheim (DE); Karl Greiner, Muehlheim (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 225 days.

This patent is subject to a terminal disclaimer.

(21) Appl. No.: 17/091,701

(22) Filed: Nov. 6, 2020

(65) Prior Publication Data
US 2021/0052312 A1 Feb. 25, 2021

Related U.S. Application Data (63) Continuation of application No. 15/808,141, filed on Nov. 9, 2017, now Pat. No. 10,856,921.

(30) Foreign Application Priority Data

Nov. 11, 2016 (EP) .................................... 16002390

(51) Int. Cl.
*A61B 17/82* (2006.01)
*A61B 90/00* (2016.01)
(Continued)

(52) U.S. Cl.
CPC ........ *A61B 17/823* (2013.01); *A61B 17/8076* (2013.01); *A61B 17/82* (2013.01);
(Continued)

(58) Field of Classification Search
CPC ....... A61B 17/82; A61B 17/823; A61B 17/84; A61B 17/842; A61B 17/844
See application file for complete search history.

(56) References Cited

U.S. PATENT DOCUMENTS

| 1,616,232 A | | 2/1927 | Roberts et al. | |
| 3,469,573 A | * | 9/1969 | Florio | A61B 17/82 606/74 |

(Continued)

FOREIGN PATENT DOCUMENTS

| CA | 2286111 A1 | 10/1998 |
| CA | 2439094 A1 | 9/2002 |

(Continued)

OTHER PUBLICATIONS

European Search Report for Application No. EP16002390.9 dated Mar. 31, 2017.
European Search Report for EP 13003896.1 dated Jul. 17, 2014.
(Continued)

*Primary Examiner* — Anu Ramana
(74) *Attorney, Agent, or Firm* — Lerner, David, Littenberg, Krumholz & Mentlik, LLP (57) ABSTRACT

Disclosed herein is an implant for bone fixation comprising an elongated member configured to be wound around bone parts that are to be fixed, an engagement member coupled to the elongated member and configured to engage a portion of the elongated member so as to secure the implant in a loop around the bone parts, and a fastening member arranged between and coupled to the elongated member and the engagement member. The fastening member comprises at least two separate pieces each comprising one opening for receiving a bone fastener, wherein the separate pieces are coupled to each other by a material having a lower material strength than a material from which the separate pieces are made.

20 Claims, 6 Drawing Sheets (51) Int. Cl.
    *A61B 17/00*           (2006.01)
    *A61B 17/80*           (2006.01)
    *A61B 17/84*           (2006.01)

(52) U.S. Cl.
    CPC ... *A61B 17/842* (2013.01); *A61B 2017/00526* (2013.01); *A61B 2090/037* (2016.02); *A61B 2090/0807* (2016.02)

(56) References Cited

U.S. PATENT DOCUMENTS

| | | | | |
|---|---|---|---|---|
| 3,887,965 | A * | 6/1975 | Schuplin | B65D 63/1063 248/74.3 |
| 3,926,193 | A | 12/1975 | Hasson | |
| 3,991,444 | A * | 11/1976 | Bailey | B65D 63/1063 24/16 PB |
| 4,003,106 | A * | 1/1977 | Schumacher | B65D 63/1063 24/16 PB |
| 4,119,091 | A | 10/1978 | Partridge | |
| 4,135,749 | A * | 1/1979 | Caveney | B65D 63/1063 24/16 PB |
| 4,136,148 | A * | 1/1979 | Joyce | F16L 3/2332 264/291 |
| 4,201,215 | A | 5/1980 | Crossett et al. | |
| 4,279,248 | A | 7/1981 | Gabbay | |
| 4,473,524 | A * | 9/1984 | Paradis | B29C 45/0055 264/296 |
| 4,512,346 | A | 4/1985 | Lemole | |
| 4,535,764 | A * | 8/1985 | Ebert | A61B 17/06 24/23 EE |
| 4,583,541 | A | 4/1986 | Barry | |
| 4,802,477 | A | 2/1989 | Gabbay | |
| 4,874,370 | A * | 10/1989 | Heimerl | A61M 3/0279 604/93.01 |
| 4,944,753 | A | 7/1990 | Burgess et al. | |
| 5,047,034 | A | 9/1991 | Sohngen | |
| 5,053,212 | A | 10/1991 | Constantz et al. | |
| 5,139,498 | A | 8/1992 | Astudillo Ley | |
| 5,146,654 | A | 9/1992 | Caveney et al. | |
| 5,164,187 | A | 11/1992 | Constantz et al. | |
| 5,188,670 | A | 2/1993 | Constantz | |
| 5,279,831 | A | 1/1994 | Constantz et al. | |
| 5,417,698 | A | 5/1995 | Green et al. | |
| 5,549,619 | A | 8/1996 | Peters et al. | |
| 5,653,711 | A | 8/1997 | Hayano et al. | |
| 5,827,286 | A | 10/1998 | Incavo et al. | |
| 5,941,881 | A | 8/1999 | Barnes | |
| 5,964,763 | A | 10/1999 | Incavo et al. | |
| 5,964,932 | A | 10/1999 | Ison et al. | |
| 5,968,253 | A | 10/1999 | Poser et al. | |
| 6,007,538 | A | 12/1999 | Levin | |
| 6,051,007 | A | 4/2000 | Hogendijk et al. | |
| 6,053,970 | A | 4/2000 | Ison et al. | |
| 6,093,201 | A | 7/2000 | Cooper et al. | |
| 6,200,318 | B1 | 3/2001 | Har-Shai et al. | |
| 6,217,580 | B1 | 4/2001 | Levin | |
| 6,302,899 | B1 | 10/2001 | Johnson et al. | |
| 6,540,769 | B1 | 4/2003 | Miller, III | |
| 6,558,709 | B2 | 5/2003 | Higham | |
| 6,596,338 | B2 | 7/2003 | Scott et al. | |
| 6,821,528 | B2 | 11/2004 | Scott et al. | |
| 6,872,210 | B2 | 3/2005 | Hearn | |
| 6,969,398 | B2 | 11/2005 | Stevens et al. | |
| 7,017,237 | B2 * | 3/2006 | Magno, Jr. | F16L 3/2334 24/16 PB |
| 7,033,377 | B2 | 4/2006 | Miller, III | |
| 7,635,364 | B2 | 12/2009 | Barrall et al. | |
| 7,695,473 | B2 | 4/2010 | Ralph et al. | |
| 7,730,592 | B2 * | 6/2010 | Krisel | B65D 63/1081 24/16 PB |
| 7,740,649 | B2 | 6/2010 | Mosca et al. | |
| 7,871,411 | B2 | 1/2011 | Grevious | |
| 7,934,297 | B2 * | 5/2011 | Williams | B65D 63/1072 292/307 A |
| 8,221,421 | B2 | 7/2012 | Hearn | |
| 8,460,295 | B2 | 6/2013 | McClellan et al. | |
| 8,486,114 | B2 | 7/2013 | Gillard et al. | |
| 9,358,054 | B2 | 6/2016 | Garcia et al. | |
| 9,474,553 | B2 | 10/2016 | Koch | |
| 10,292,742 | B2 | 5/2019 | Knoepfle et al. | |
| 10,433,889 | B2 | 10/2019 | Knoepfle | |
| 11,259,853 | B2 * | 3/2022 | Knoepfle | A61B 17/8076 |
| 2002/0077659 | A1 | 6/2002 | Johnson et al. | |
| 2002/0128654 | A1 | 9/2002 | Steger et al. | |
| 2002/0143336 | A1 | 10/2002 | Hearn | |
| 2003/0049324 | A1 | 3/2003 | Vogt et al. | |
| 2003/0077381 | A1 | 4/2003 | Scott et al. | |
| 2003/0083694 | A1 | 5/2003 | Miller | |
| 2003/0212399 | A1 | 11/2003 | Dinh et al. | |
| 2004/0010256 | A1 | 1/2004 | Gabbay | |
| 2004/0133206 | A1 | 7/2004 | Stevens et al. | |
| 2005/0070928 | A1 | 3/2005 | Heino et al. | |
| 2005/0124996 | A1 | 6/2005 | Hearn | |
| 2005/0267475 | A1 | 12/2005 | Miller | |
| 2005/0288674 | A1 | 12/2005 | Golobek | |
| 2006/0116683 | A1 | 6/2006 | Barrall et al. | |
| 2006/0122611 | A1 | 6/2006 | Morales et al. | |
| 2006/0134160 | A1 | 6/2006 | Troczynski et al. | |
| 2006/0161161 | A1 | 7/2006 | Shifrin et al. | |
| 2006/0195101 | A1 | 8/2006 | Stevens | |
| 2006/0259141 | A1 | 11/2006 | Roman et al. | |
| 2006/0276794 | A1 | 12/2006 | Stern | |
| 2007/0038218 | A1 | 2/2007 | Grevious | |
| 2007/0043371 | A1 | 2/2007 | Teague et al. | |
| 2007/0213832 | A1 | 9/2007 | Wen | |
| 2007/0259101 | A1 | 11/2007 | Kleiner et al. | |
| 2008/0154312 | A1 | 6/2008 | Colleran et al. | |
| 2008/0221578 | A1 | 9/2008 | Zeitani | |
| 2008/0306579 | A1 | 12/2008 | Dolan et al. | |
| 2009/0118774 | A1 | 5/2009 | Miller, III | |
| 2009/0118775 | A1 | 5/2009 | Burke | |
| 2009/0138054 | A1 | 5/2009 | Teague et al. | |
| 2009/0234357 | A1 | 9/2009 | Morales et al. | |
| 2009/0234358 | A1 | 9/2009 | Morales et al. | |
| 2009/0248091 | A1 | 10/2009 | Teague et al. | |
| 2009/0269480 | A1 | 10/2009 | Berglund | |
| 2010/0094294 | A1 | 4/2010 | Gillard et al. | |
| 2010/0179600 | A1 | 7/2010 | Steger et al. | |
| 2010/0305569 | A1 | 12/2010 | Leuenberger et al. | |
| 2010/0318085 | A1 | 12/2010 | Austin et al. | |
| 2011/0015681 | A1 | 1/2011 | Elsbury | |
| 2011/0125193 | A1 | 5/2011 | Grevious | |
| 2011/0166612 | A1 | 7/2011 | Bardaji Pascual et al. | |
| 2011/0295257 | A1 | 12/2011 | McClellan et al. | |
| 2011/0313474 | A1 | 12/2011 | Gabele | |
| 2013/0261625 | A1 | 10/2013 | Koch et al. | |
| 2013/0338719 | A1 | 12/2013 | Madjarov | |
| 2014/0100573 | A1 | 4/2014 | Llas Vargas et al. | |
| 2014/0142638 | A1 | 5/2014 | Goodwin et al. | |
| 2015/0045794 | A1 | 2/2015 | Garcia et al. | |

FOREIGN PATENT DOCUMENTS

| | | |
|---|---|---|
| CN | 101537208 A | 9/2009 |
| CN | 202235628 U | 5/2012 |
| DE | 202004021763 U1 | 9/2010 |
| DE | 102010021737 A1 | 11/2011 |
| DE | 102011109677 A1 | 2/2013 |
| EP | 0238219 A1 | 9/1987 |
| EP | 0597259 A2 | 5/1994 |
| EP | 0608592 A1 | 8/1994 |
| EP | 0806212 A1 | 11/1997 |
| EP | 0608592 B1 | 8/1998 |
| EP | 1099416 A2 | 5/2001 |
| EP | 1121058 A1 | 8/2001 |
| EP | 1521552 A1 | 4/2005 |
| EP | 1365693 B1 | 1/2006 |
| EP | 1429674 B1 | 3/2006 |
| EP | 1654994 A1 | 5/2006 |
| EP | 1691702 A1 | 8/2006 |
| EP | 1732460 B1 | 5/2010 |
| EP | 1885268 B1 | 7/2010 |
| EP | 2063799 B1 | 9/2010 |

(56) References Cited

FOREIGN PATENT DOCUMENTS

| | | |
|---|---|---|
| EP | 2367489 A1 | 9/2011 |
| EP | 1748738 B1 | 10/2011 |
| EP | 3042622 A1 | 7/2016 |
| WO | 9004366 A1 | 5/1990 |
| WO | 9505782 A1 | 3/1995 |
| WO | 9844850 A1 | 10/1998 |
| WO | 0022992 A1 | 4/2000 |
| WO | 02/067795 A1 | 9/2002 |
| WO | 03037201 A1 | 5/2003 |
| WO | 2004006784 A1 | 1/2004 |
| WO | 2004078218 A2 | 9/2004 |
| WO | 2005055844 A1 | 6/2005 |
| WO | 2005117726 A2 | 12/2005 |
| WO | 2006135935 A1 | 12/2006 |
| WO | 2007084238 A2 | 7/2007 |
| WO | 2008034537 A1 | 3/2008 |
| WO | 2009100792 A2 | 8/2009 |
| WO | 2010024946 A1 | 3/2010 |
| WO | 2010042946 A1 | 4/2010 |
| WO | 2010126436 A1 | 11/2010 |
| WO | 2011153676 A1 | 12/2011 |
| WO | 2013013218 A2 | 1/2013 |
| WO | 2013067049 A1 | 5/2013 |
| WO | 2013072576 A1 | 5/2013 |
| WO | 2014081574 A1 | 5/2014 |
| WO | 2014144479 A1 | 9/2014 |
| WO | 2015142588 A2 | 9/2015 |

OTHER PUBLICATIONS

International Search Report and Written Opinion for Application No. PCT/EP2013/066408 dated Oct. 22, 2013.

International Preliminary Report on Patentability Chapter II, for Application No. PCT/EP2013/066408 dated Sep. 25, 2015.

Extended European Search Report for Application No. 15000033.9 dated Jun. 24, 2015.

"Non-Toxic and Bio-Compatible Type 2 Titanium Anodizing", 2003, XP055117504, Retrieved from the Internet: <URL:http://www.danco.net/PDF-DOWNLOADS/TITANIUM I I. pdf>, [retrieved on May 12, 2014].

International Search Report for Application No. PCT/EP2013/068082 dated May 26, 2014.

Aberg et al, Bisphosphonate incorporation in surgical implant coatings by fast loading and co-precipitation at low drug concentralions, J Mater Sci: Mater Med (2009) 20:2053-2061.

Abtahl et al, A bisphosphonate-coating improves the fixation of metal implants in human bone, A randomized trial of dental implants, Bone 50 (2012) 1148-1151.

Sergio Allegrini Jr., et al, Hydroxyapatite grafting promotes new bone formation and osseointegration of smooth titanium implants, Ann Anat 188 (2006) 143-151.

James M Anderson, Biological Responses to Materials, Annu. Rev. Mater. Res. 2001. 31:81-110.

K.C. Baker et al, Growth, characterization and biocompatibility of bone-like calcium phosphate layers biomimetically deposited on metallic substrata, Materials Science and Engineering C 26 (2006) 1351-1360.

Brohede et al, Multifunctional implant coatings providing possibilities for fast antibiotics loading with subsequent slow release, J Mater Sci: Mater Med (2009) 20:1859-1867.

Brunski et al, Biomaterials and Biomechanics of Oral and Maxillofacial Implants: Current Status and Future Developments, The Inrtemational Journal of Oral & Maxillofacial Implants, 2000. 15-46.

F. Chai et al, Antibacterial activation of hydroxyapatite (HA) with controlled porosity by different antibiotics, Biomolecular Engineering 24 (2007) 510-514.

Johan Forsgren et al, Formation and adhesion of biomimetic hydroxyapatite deposited on titanium substrates, Acta Biomaterialia 3 (2007) 980-984.

Forsgren et al, Co-loading of bisphosphonates and antibiotics to a biomimetic hydroxyapatite coating, Biotechnol Lett (2011) 33 :1265-1268.

M.P. Ginebra et al., Calcium phosphate cements as bone drug delivery systems: A review, Journal of Controlled Release 113 (2006) 102-110.

Hetrick et al, Reducing implant-related infections: active release strategies, I Chem. Soc. Rev., 2006, 35, 780-789.

Hutson et al, Infections in Periarticular Fractures of the Lower Extremity Treated with Tensioned Wire Hybrid Fixators, Journal of Orthopaedic Trauma vol. 12, No. 3, 1998, pp. 214-218.

Lilja et al, Photocatalytic and antimicrobial properties of surgical implant coatings of titanium dioxide deposited though cathodic arc evaporation, Biotechnol Lett (2012) 34:2299-2305.

Liu et al, Water-based sol-gel synthesis of hydroxyapatite: process development, Biomaterials 22 (2001) 1721-1730.

Ma et al, Electrophoretic deposition of porous hydroxyapatite scaffold, Biomaterials 24 (2003) 3505-3510.

Mahan et al, Factors in Pin Tract Infections, Department of Orthopedic Surgery, University of Louisville, Louisville, Ky., Mar. 1991 vol. 14 No. 3 V , pp. 305-308.

Masse et al, Prevention of Pin Track Infection in External Fixation with Silver Coated Pins: Clinical and Microbiological Results, J Biomed Mater Res (Appl Biomater) 53: 600-604, 2000.

Poelstra et al, Prophylactic treatment of gram-positive and gram-negative abdominal implant infections using locally delivered polyclonal antibodies, Received: Jun. 15, 2000, pp. 206-215.

Tengvalla et al, Surface immobilized bisphosphonate improves stainless-steel screw fixation in rats, Biomaterials 25 (2004) 2133-2138.

Zilberman et al., Antibiotic-eluting medical devices for various applications, journal of Controlled Release 130 (2008) 202-215.

Ulrika Brohede et al: "Multifunctional implant coatings providing possibilities for fast antibiotics loading with subsequent slow release", Journal of Materials Science: Materials in Medicine, Kluwer Academic Publishers, BO, vol. 20, No. 9, Apr. 28 1, 2009 (Apr. 28, 2009) pp. 1859-1867, XP019730963.

Stigter M et al: "Incorporation of tobramycin into biomimetic hydroxyapatite coating on titanium", Biomaterials. Elsevier Science Publishers BV, Barking, GB, vol. 23, No. 20, Oct. 1, 2002 (Oct. 1, 2002), pp. 4143-4153. XP004370405.

Stigter M et al: "Incorporation of different antibiotics into carbonated hydroxyapatite coatings on titanium implants. release and antibiotic efficacy", Journal of Controlled Release, Elsevier, Amsterdam, NL, vol. 99, No. 1, Sep. 14, 2004 (Sep. 14, 2004). pages 127-137, XP004549075.

International Search Report for Application No. PCT/IB2014/060905 dated Jun. 26, 2014.

International Search Report for Application No. PCT/IB2014/062454 dated Sep. 29, 2014.

Synthes CMF, "Modular Sternal Cable System", 2006, 12 pages.

Sörensen et al., "Biomimetic Hydroxyapatite Coated Titanium Screws Demonstrate Rapid Implant Stabilization and Safe Removal In-Vivo", Journal of Biomaterials and Nanobiotechnology, 2015, 6, 20-35.

Sörensen et al., "Biomechanical and antibacterial properties of Tobramycin loaded hydroxyapatite coated fixation pins". Journal of Biomedical Materials Research B: Applied Biomaterials, 2014, vol. 00B, Issue 00, 12 pages.

Synthes CMF, "Sternal ZipFix System—For fast and stable fixation of the sternum", Technique Guide, 2011, 26 pages.

\* cited by examiner

IMPLANT FOR BONE FIXATION

CROSS-REFERENCE TO RELATED APPLICATION

The present application is a continuation of U.S. patent application Ser. No. 15/808,141, filed on Nov. 9, 2017, which claims priority from European Patent Application No. 16 002 390.9, filed on Nov. 11, 2016, the disclosures of which are hereby incorporated herein by reference.

TECHNICAL FIELD

The present disclosure generally relates to bone fixation. In particular, an implant for bone fixation is described.

BACKGROUND OF THE INVENTION

Various surgical procedures require the surgeon to access the thoracic region of a patient. A known approach to access the thoracic region is to cut the sternum in two parts and separate these two parts from each other for gaining access to the thoracic region. After completion of the surgical procedure, the separated parts of the sternum are brought back to their initial positions and fixed, for example, with a bone plate attached to the sternum parts or a wire tensioned around the circumference of the sternum.

After the thoracic procedure such as, for example, a bypass operation has been carried out on a patient and the sternum parts have been fixed using a suitable fixation assembly, the patient is normally kept under surveillance. If it is detected that the surgical procedure has failed or that complications occur, it may be desirable for the surgeon to again open the fixation system for accessing the thoracic region. The time required for this opening procedure may be critical for the patient's health and even life.

In other situations, a cable or wire tensioned around the sternum parts (so-called "primary closure") might become loose or break due to the load applied to the thoracic region of the patient. In such cases, the sternum part fixation may need to be stabilized by, for example, a bone plate (so-called "secondary closure").

Similar or related problems occur in connection with other surgical procedures in which two or more bone parts need to be fixed.

EP 0 597 259 A2 discloses a closure element to be looped around a human sternum. The closure element comprises a strap, which is inserted through and retained by a tightening plate.

U.S. Pat. No. 8,460,295 B2 discloses a sternum repair device including a central body and a plurality of bands extending from the central body. The bands are wrapped around the sternum to keep the sternum parts together. The central body includes a view window, which is used by a surgeon to line up the device during installation on the sternum.

WO 2010/042946 A1 discloses a cerclage system including a cable that encircles the sternum parts and a bone plate having channels to receive segments of the cable. The bone plate further includes a pair of locking studs to lock the cable within the channels to the bone plate.

EP 0 608 592 B1 discloses an assembly for banding a sternum. The assembly comprises an elongated flexible band, a needle at one end of the band and a buckle proximate the other end of the band. A main section of the band includes a plurality of spaced apart slots, which can engage at a locking mechanism.

BRIEF SUMMARY OF THE INVENTION

An implant for bone fixation is provided that comprises an elongated member configured to be wound around bone parts that are to be fixed, an engagement member coupled to the elongated member and configured to engage a portion of the elongated member so as to secure the implant in a loop around the bone parts and a fastening member arranged between and coupled to the elongated member and the engagement member. The fastening member comprises at least two separate pieces each comprising at least one opening for receiving a bone fastener, and the separate pieces are coupled to each other by a material having a lower material strength than a material from which the separate pieces are made.

Each individual piece may have a lower surface directed towards bone in an implanted state and an upper surface. The lower surface and the upper surface may extend parallel to each other. The one or more openings of each piece may extend from the upper surface to the lower surface.

The separate pieces may be coupled in a distance to each other. The distance may range between 1 mm and 50 mm (e.g., between 3 mm and 25 mm).

The separate pieces may be substantially aligned with a longitudinal extension of the implant in a straight, unwound state of the implant. As an example, the centers of the openings may be located on a line that coincides with the longitudinal extension of the elongated member in its straight, unwound state.

The separate pieces may be plates made from a metallic material. As an example, the pieces may be made from titanium or stainless steel.

The material coupling the separate pieces together may be identical to the material from which the elongated member and/or the engagement member is made. The material coupling the separate pieces to each other may be a polymeric material (e.g., PEEK). The polymeric material may be bio-degradable.

The implant may comprise at least one visual indicator in a region of lower material strength between the separated pieces. The visual indicator may indicate where to cut the implant for quickly separating the bone parts.

Generally, a first one of the separate pieces may be located in the implant for attachment to a first bone part and a second one of the separate pieces may be located in the implant for attachment to a second bone parts. The bone parts may belong to a previously separated sternum bone.

The fastening member may be coupled to at least one of the elongated member and the engagement member by injection molding. Additionally, or in the alternative, the implant may be an injection-molded part. The visual indicator may be defined by a portion of the fastening member that remains exposed from injection molding, or otherwise.

The elongated member may have a bone-contacting surface and at least one first side extending substantially perpendicular to the bone-contacting surface and comprising a plurality of engagement features along its longitudinal extension, and the engagement member may comprise at least one complementary deflectable engagement feature configured to engage at least one of the engagement features. It should be noted that this engagement aspect can be implemented in any implant for bone fixation that comprises an elongated member configured to be wound around bone parts that are to be fixed and an engagement member coupled to the elongated member and configured to engage a portion of the elongated member so as to secure the implant in a loop around the bone parts. In other words, such an implant may or may not comprise a fastening member arranged between and coupled to the elongated member and the engagement member. Moreover, if a fastening member is provided it may comprise one or two pieces (e.g., plates) with one or more openings for receiving a bone fastener as generally described herein.

The elongated member may comprise a second side opposite to the first side. In such a case the engagement features of the elongated member may be arranged on both sides of the elongated member.

The elongated member may comprise a lateral step that defines the first side. In such a case the engagement features of the elongated member may be arranged within the lateral step.

The engagement member may comprise at least one shoulder engaging with the lateral step. The shoulder and the at least one complementary deflectable engagement feature may or may not be offset in a longitudinal extension of the engagement member. In some variants, the shoulder may be closer to the elongated member than the at least one complementary deflectable engagement feature.

The implant may have a groove on a surface opposite the bone-contacting surface, which groove extends in a direction substantially perpendicular to the longitudinal extension of the implant between the engagement member and the elongated member. As an example, the groove may extend between the engagement member and the fastening member. Additionally, or alternatively, the groove may extend between the fastening member and the elongated member.

The engagement member and the fastening member may be arranged within a common plane (e.g., in a straight, unwound state of the implant). The engagement member may comprise at least one deflectable engagement feature that substantially lies within the common plane. Additionally, or in the alternative, the deflectable engagement feature may be deflectable within a plane which is parallel or orthogonal to the bone-contacting surface of the implant (e.g., of the elongated member, in a straight, unwound state thereof).

The engagement feature of the engagement member may be distanced from the bone-contacting surface (e.g., in a section of the engagement feature that is resilient in a top to bottom direction of the implant). The arrangement may be such that a maximum resilient displacement of the engagement feature caused by the engagement features of the engagement features portion stops before reaching a plane defined by the bone-contacting surface of the engagement member.

A top surface of the separate pieces in a bottom to top direction of the implant may form the maximum extension of the implant in a bottom to top direction of the implant, in a straight, unwound state of the implant. Additionally, or in the alternative, a bottom surface of the separate pieces in a top to bottom direction of the implant may form the maximum extension of the implant in a top to bottom direction of the implant, in a straight, unwound state of the implant.

BRIEF DESCRIPTION OF THE DRAWINGS

The above and other features, aspects and advantages of the present disclosure will now be explained with reference to the following description of exemplary embodiments and the accompanying drawings, wherein:

FIG. 3b is an enlarged perspective top view of the engagement member portion and the fastening member portion shown in FIG. 3a;

DETAILED DESCRIPTION

In the following description, exemplary embodiments of a bone fixation implant will be explained with reference to the drawings. The same or similar reference numerals will be used to denote the same or similar structural features.

Figure 1:
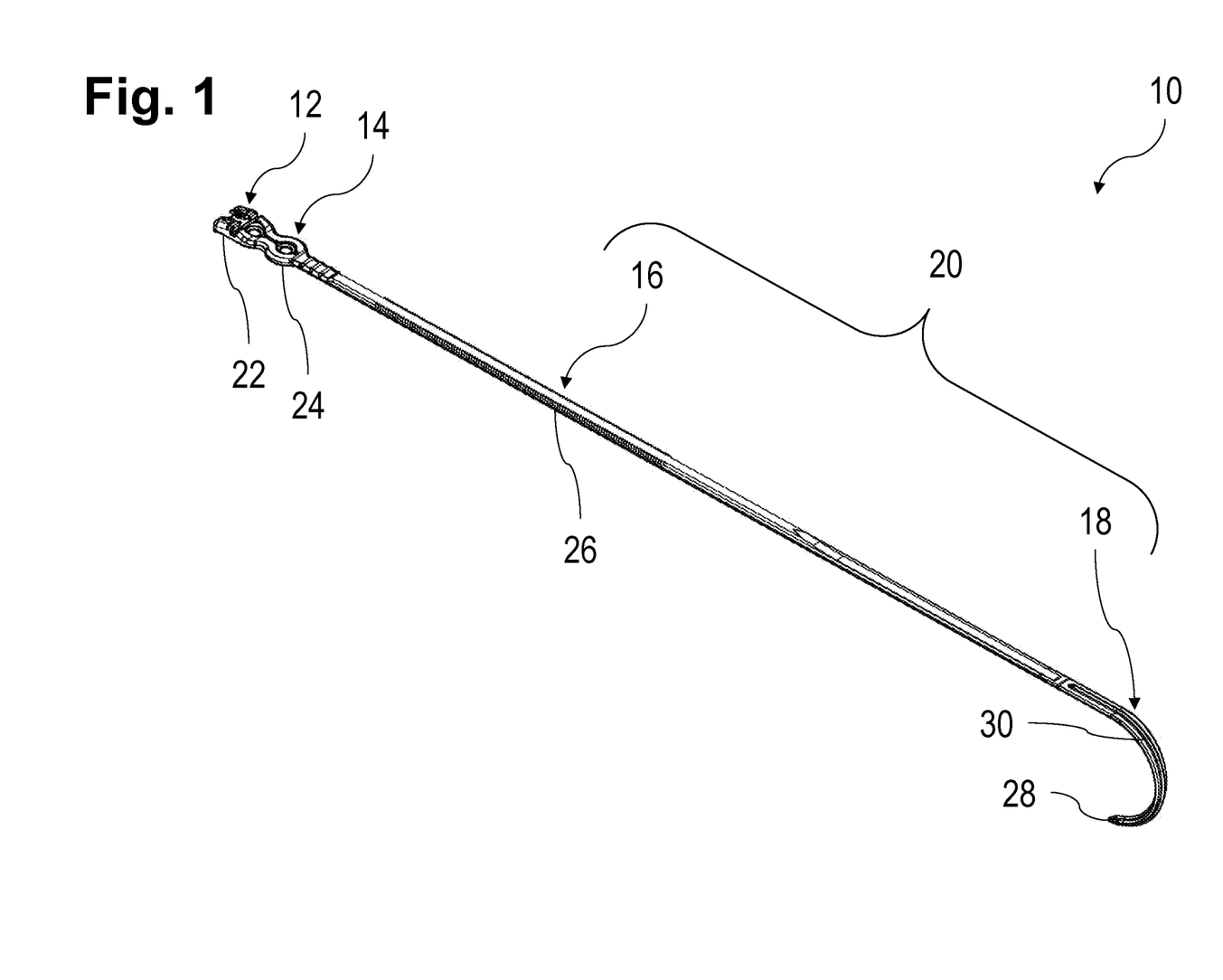
FIG. 1 is a perspective top view of an embodiment of an implant for bone fixation with an engagement member portion, a fastening member portion, an engagement features portion and a tip portion.

In the embodiment shown in FIG. 1, the implant 10 is configured and dimensioned for fixing bone parts of a sternum. It will be appreciated that the present disclosure is not limited to this surgical indication. Rather, the present disclosure can also be applied in connection with fixing bone parts in other regions of the human anatomy, possibly with suitably adapted configurations and dimensions.

FIG. 1 shows a perspective top view of an embodiment of an injection-molded (e.g., from a polymeric material such as PEEK) implant 10 for bone fixation, wherein the implant 10 preferably has a length of approximately 10 to 35 cm, with an engagement member portion 12, a fastening member portion 14, an engagement features portion 16 and an optional tip portion 18. The engagement features portion 16 and the tip portion 18 form together an elongated member 20 configured to be wound in a loop around bone parts that are to be fixed. The tip portion 18 may be configured to be separated from the remainder of the implant 10, possibly with a portion of the engagement features portion 16, after the implant 10 has been placed at the patient.

The engagement member portion 12 comprises an engagement member 22, which is coupled to the elongated member 20 and configured to engage the engagement features portion 16 so as to secure the implant 10 in a loop around the bone parts. The fastening member portion 14 comprises a fastening member 24, which is arranged between and coupled to the elongated member 20 and the engagement member 22 by injection molding. The fastening member portion 14 and the fastening member 24 are described in greater detail with reference to FIGS. 3b and 3c below.

The engagement features portion 16 comprises a plurality of engagement features 26 along its longitudinal extension. The tip portion 18 comprises a blunt tip 28 and is enforced by longitudinal rips 30, preferably extending from opposite sides of the tip portion 18, such that the tip portion 18 can be more reliably guided around bone parts that are to be fixed, thereby supporting a proper placement of the implant 10. For the latter, a hook shape of the tip portion 18 may be advantageous, depending on the surgical indication. The tip portion 18 may be made from a material different form the material of the engagement member portion 12 and the engagement features portion 16. As example, the tip portion 18 may be made from a metallic material such as titanium or stainless steel. The tip portion 18 may be injection-molded to the engagement features portion 16

Figure 2:
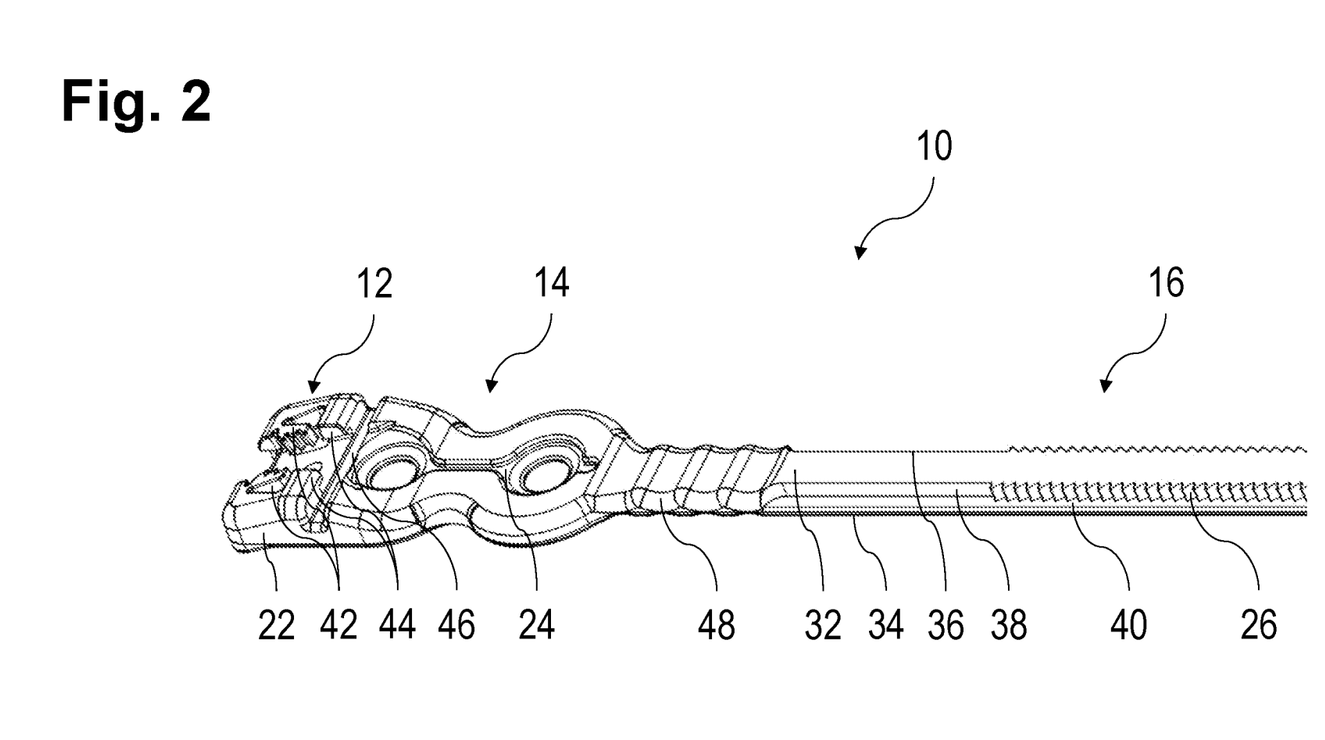
FIG. 2 is an enlarged perspective top view of the engagement member portion, the fastening member portion and a part of the engagement features portion of the implant shown in FIG. 1.

FIG. 2 shows an enlarged perspective top view of the engagement member portion 12, the fastening member portion 14 and a part of the engagement features portion 16 of the implant 10 shown in FIG. 1. The implant 10 has a top surface 32, a bone-contacting bottom 34, which is opposite to the top surface 32, and first and second sides 36, 38 opposite to each other, which extend substantially perpendicular to the bone-contacting bottom 34, also referred to as a bone-contacting surface. The top 32 and bottom 34 define a top to bottom direction of the implant 10. The engagement features portion 16 comprises the engagement features 26 on the first and second side 36, 38. These engagement features 26 are arranged within a lateral step 40, which defines the respective side 36, 38.

The engagement member 22 comprises two complementary deflectable engagement features 42, which are configured to engage at least one of the engagement features 26. The engagement member 22 further comprises two shoulders 44 engaging with the top surface 32 of the engagement features portion 16, when the engagement features portion 16 is wound in a direction of the bone-contacting bottom 34 and passed through the engagement member 22 further towards the fastening member portion 14. This engagement solution results in a low height of the engagement member portion 12, which is often desirable from a surgical perspective.

Alternatively or additionally, the shoulders 44 may engage with the lateral steps 40 on both sides 36, 38, which further reduces the height of the engagement member portion 12 in the top to bottom direction and/or further improves the guidance of the engagement features portion 16 through the engagement member portion 12, such that an engagement between at least one of the engagement features 26 of the engagement features portion 16 and the deflectable engagement features 42 of the engagement member portion 12 is ensured.

The shoulders 44 and the deflectable engagement features 42 are offset in a longitudinal extension of the engagement member portion 12, wherein the shoulders 44 are closer to the elongated member 20 than the deflectable engagement features 42, which further improves the engagement reliability between at least one of the engagement features 26 of the engagement features portion 16 and the deflectable engagement features 42 of the engagement member portion 12.

Alternatively, one shoulder 44 is also sufficient to ensure the above mentioned engagement. Likewise, only one side 36 extending substantially perpendicular to the bone-contacting bottom 34 and being defined by a lateral step 40 is sufficient. In other words, such an engagement features portion 16 will have a right triangular cross-section perpendicular to the longitudinal extension of the elongated member 20 with one cathetus being part of the bone-contacting bottom 34 and the other cathetus being the side 36. In this case, the shoulder 44 will engage with the hypotenuse of the triangle. As a matter of course, the cross-section may alternatively have any other shape, for example that of a rectangle, circle, oval, trapezium, diamond, pentagon, and so forth.

As a further alternative, the step 40 may be covered by the top surface 32, such that the step 40 has the shape of a groove in at least one of the sides 36, 38, which reduces the risk of damaging human tissue during the insertion and winding of the implant 10 around bone parts that are to be fixed.

Further, a groove 46 is formed between the engagement member portion 12 and the fastening member portion 14 on the top surface 32 opposite the bone-contacting bottom 34, such that the groove 46 extends in a direction substantially perpendicular to the longitudinal extension of the elongated member 20.

The engagement member 22 and the fastening member 24 are arranged within a common plane, wherein the deflectable engagement features 42 substantially lie within the common plane and are deflectable within a plane which is parallel to the bone-contacting bottom 34 of the elongated member 20 in a straight, unwound state thereof.

A further bending section 48 is provided between the fastening member portion 14 and the engagement features portion 16 as a further part of the implant 10. The bending section 48 has a greater flexibility compared to the entire elongated member 20 and is comprised of multiple grooves. Of course, the bending section 48 may have a single groove similar to the groove 46 formed between the engagement member portion 12 and the fastening member portion 14.

Figure 3A:
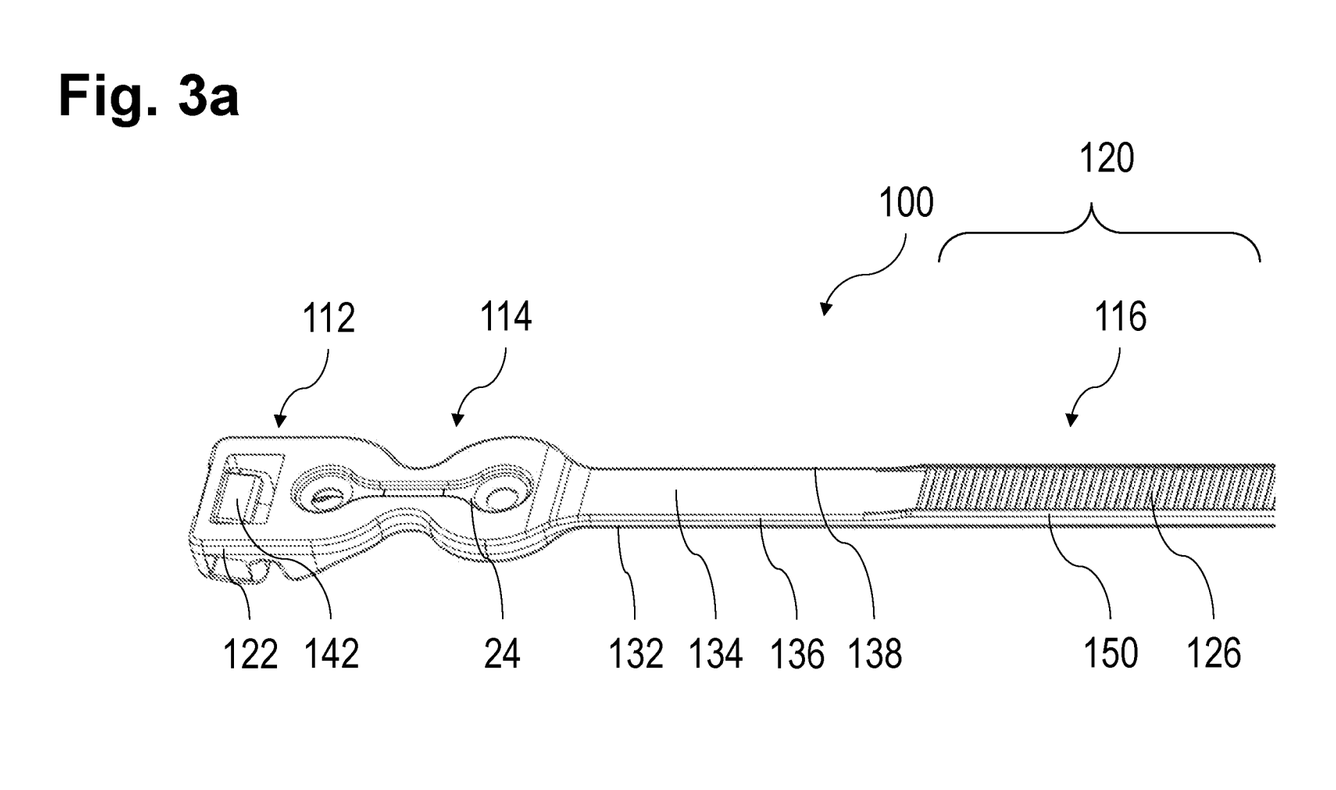
FIG. 3a is an enlarged perspective bottom view of a further engagement member portion, fastening member portion and a part of an engagement features portion of another embodiment of an implant for bone fixation.

FIG. 3a shows an enlarged perspective bottom view of a further engagement member portion 112, fastening member portion 114 and part of an engagement features portion 116 of another embodiment of an implant 100 for bone fixation. This embodiment differs from the previous one. First of all, the engagement features 126 of the engagement features portion 116 are arranged on the bone-contacting bottom 134 only, such that the top surface 132 and the sides 136, 138 can remain uniformly shaped along the elongated member 120. Here, the engagement features 126 protrude from the bone-contacting bottom 134 and are enclosed by an enclosure 150 which also protrudes from the bone-contacting bottom 134 and reduces the risk of damaging human tissue during the insertion and winding of the implant 100 around bone parts that are to be fixed. For that purpose, the engagement features 126 may alternatively be within a longitudinal groove formed in the bone-contacting bottom 134, similar to the groove provided in the previous embodiment for the sides 36, 38.

In this embodiment, the bending section 48 is missing, but could easily be added and would have the same purpose as in the previous embodiment.

The engagement member portion 112 comprises an engagement member 122 with a single engagement feature 142, which is deflectable within a plane which is orthogonal to the bone-contacting bottom 134 of the elongated member 120 in a straight, unwound state thereof. The engagement member portion 112 is further described with reference to FIGS. 3a to 3c.

Figure 3B:
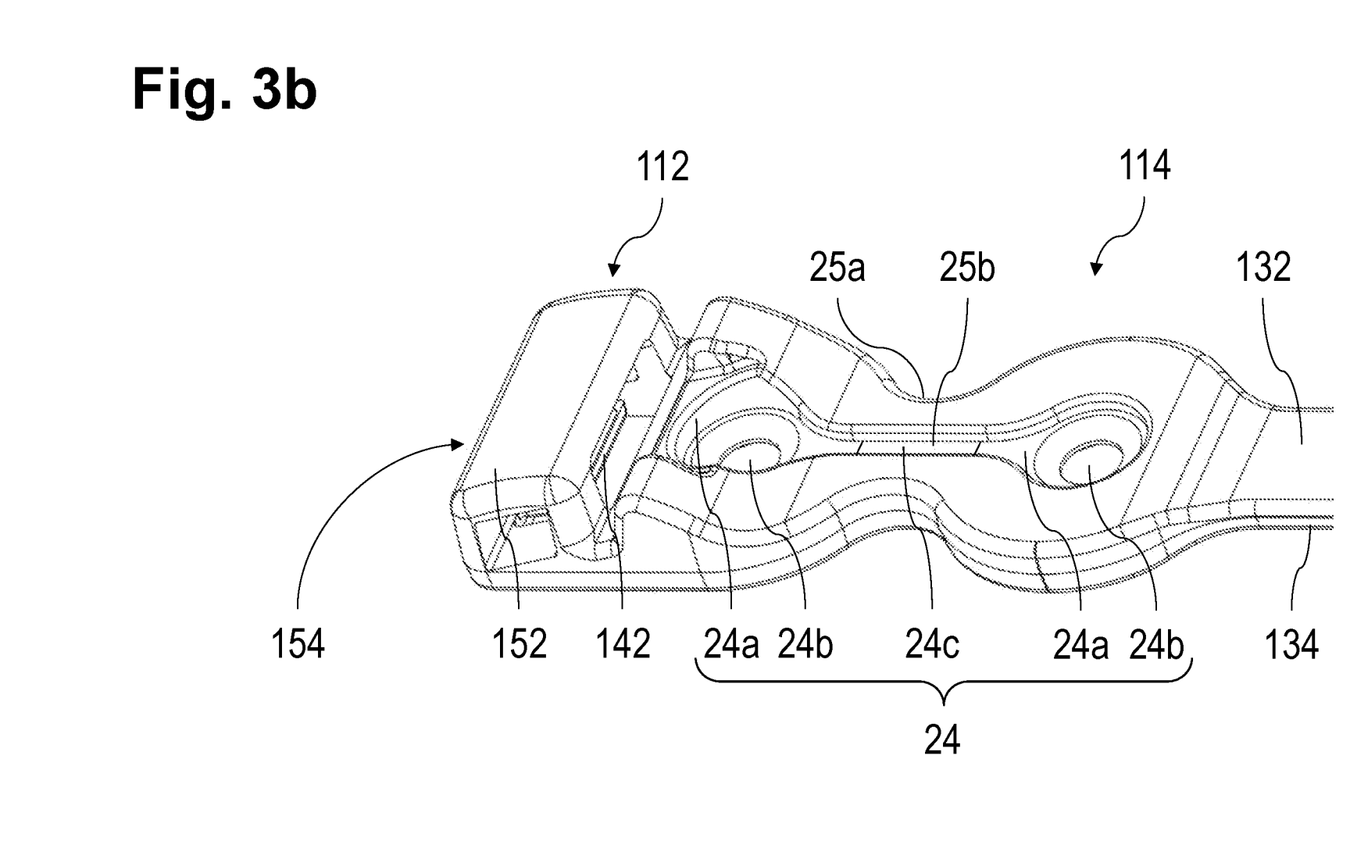

FIG. 3b shows an enlarged perspective top view of the engagement member portion 112 and the fastening member portion 114 shown in FIG. 3a. Here the engagement member portion 112 comprises a cover 152 covering the engagement feature 142 and forming a passage 154 for the elongated member 120 after being wound around bone parts that are to be fixed and passed through the passage 154 with the engagement features 126 of the engagement features portion 116 facing the engagement feature 142 of the engagement member 122.

As illustrated in FIG. 3b, the fastening member 24 comprises two separate pieces 24a made from a metallic material (e.g., stainless steel, titanium, or a titanium alloy), each comprising one opening 24b for receiving a bone fastener, such as a bone screw or bone pin. These pieces 24a are coupled to each other by a coupling portion 24c made from a polymeric material, which has a lower material strength than the material from which the pieces 24a of the fastening member 24 are made. The coupling portion 24c couples the pieces 24a in a distance from each other along the longitudinal extension of the implant 100.

The separate pieces 24a are substantially aligned with a longitudinal extension of the implant 100, preferably of the elongated member 120, in a straight, unwound state thereof. Visual indicators 25a, 25b are provided between the pieces 24a, either in the form of an indentation 25a in the outer shape of the fastening member portion 114 and/or in the form of a portion 25b of the fastening member portion 114 that remains exposed from injection molding. The purpose of these visual indicators 25a, 25b is to indicate the region of the fastening member 25 of reduced mechanical strength to be cut in order to detach the implant 100 after implantation. As such, the visual indicators 25a, 25b indicate the region of the fastening member 24 that is easiest to sever by a surgical cutter in order to detach the implant 100. Of course, only one of the visual indicators 25a, 25b is also sufficient. In some cases even no visual indicator 25a, 25b may be provided.

The separate pieces 24a may each have the appearance of a bone plate with an upper surface and a lower surface that extends in parallel to the lower surface, wherein the respective opening 24b extends between the upper surface and the lower surface. Each opening 24b is defined by a tapering circumferential lip of the respective piece 24a. The lip is configured to cooperate with a thread provided at a head of a complementary bone fastener so as to lock the bone fastener in at a selected angular relationship with the respective piece 24a. While each piece 24a shown in the drawings comprises only one opening 24b, it will be appreciated that more openings per piece 24a may be provided.

Figure 3C:
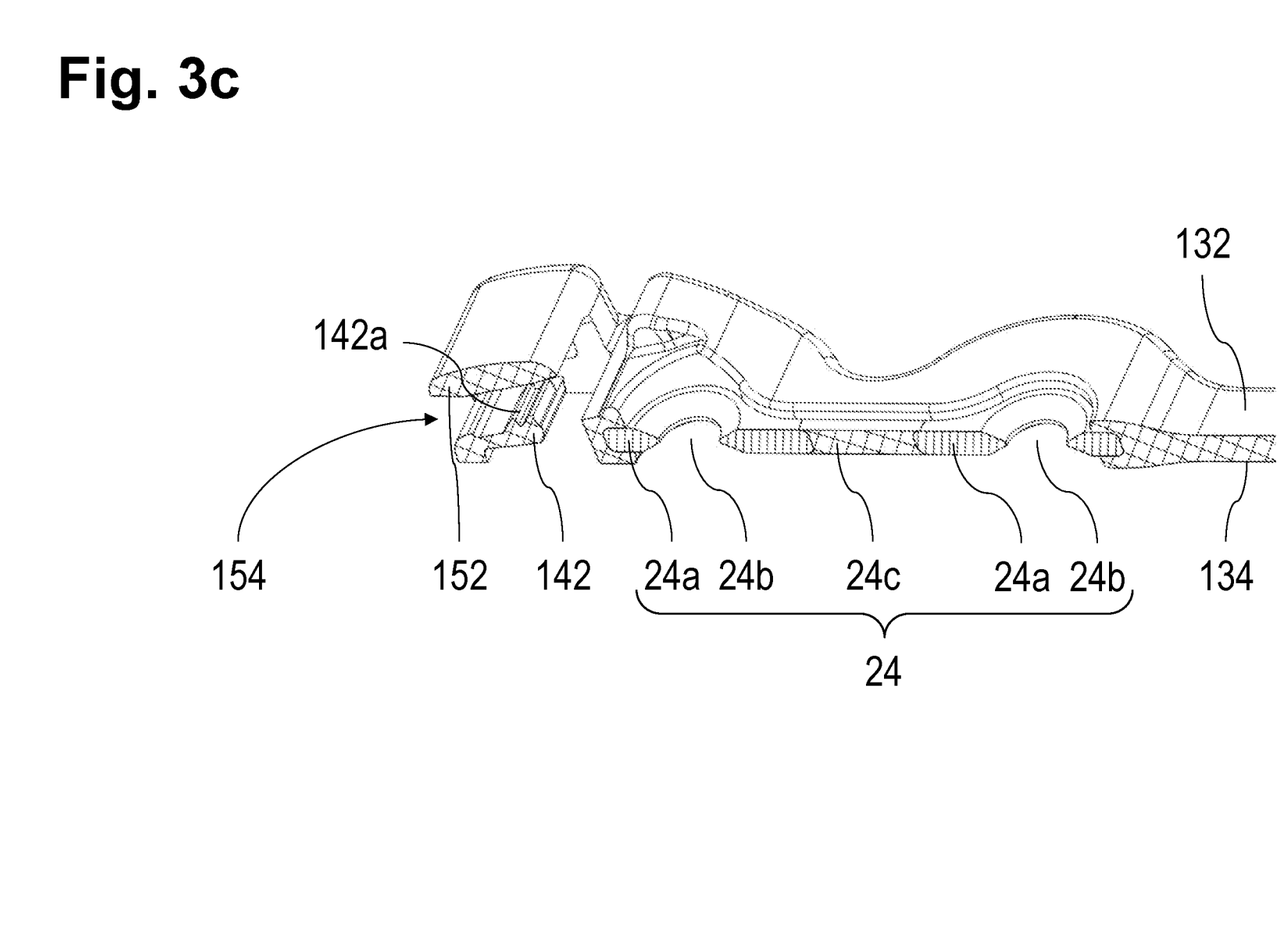
FIG. 3c is a perspective cross-sectional view of the engagement member portion and the fastening member portion shown in FIG. 3b along the longitudinal extension center of the implant for bone fixation.

FIG. 3c shows a perspective cross-sectional view of the engagement member portion 112 and the fastening member portion 114 shown in FIG. 3b along the longitudinal extension center of the implant 100 for bone fixation. Here, it is visible that a free end of the engagement feature 142 comprises two engagement teeth 142a directed towards the cover 152, while the engagement feature 142 substantially extends in the longitudinal extension of the implant 100 towards the fastening member portion 114 in a straight, unwound state of the implant 100. Or course, the engagement feature 142 may be a resilient membrane, which spans continuously to the fastening member portion 114 with the engagement teeth 142a being arranged in a center in a longitudinal direction of the implant 100. Of course, instead of two engagement teeth 142a, one as well as more than two is also a possibility in any of the embodiments.

Figure 3D:
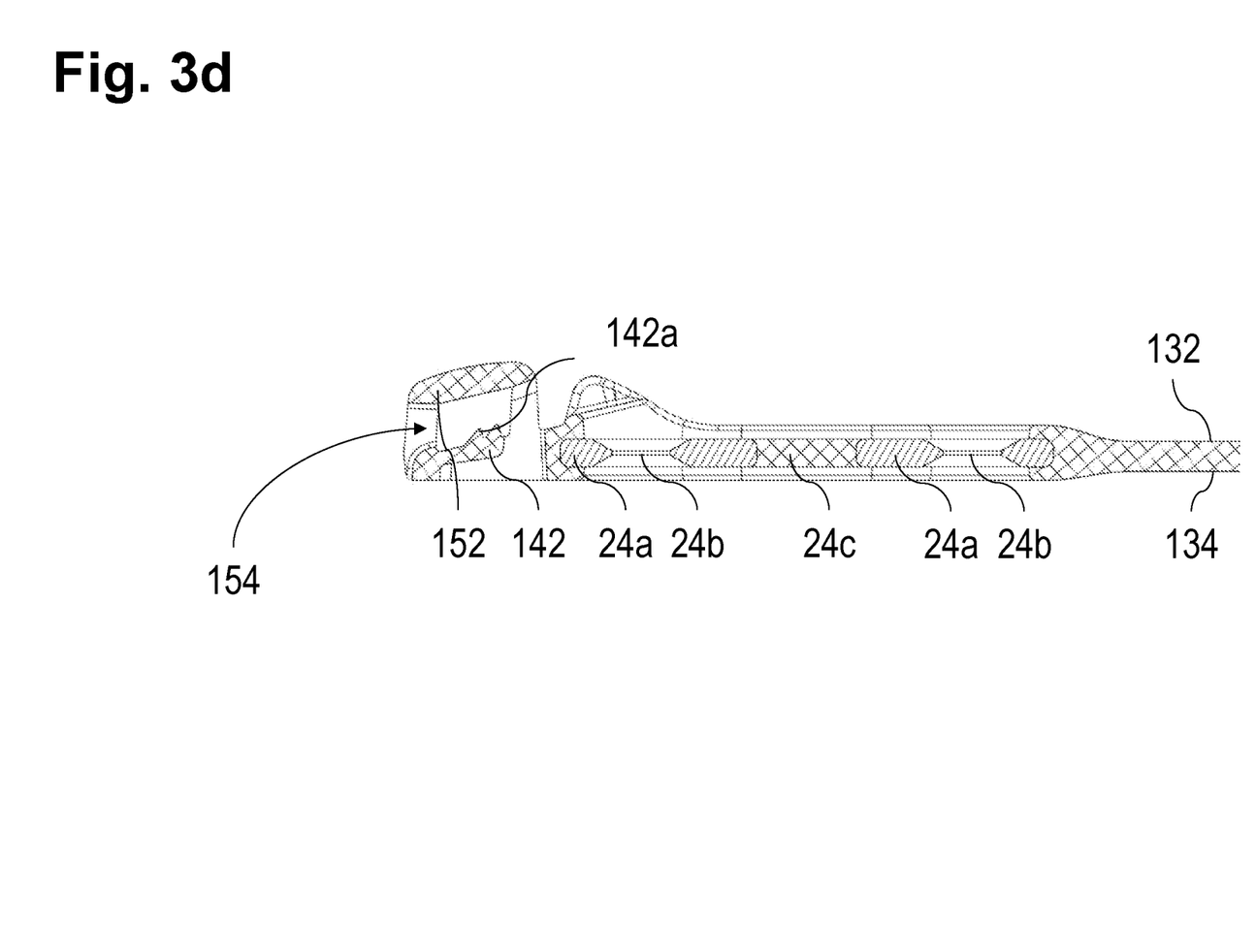
FIG. 3d is a side cross-sectional view of the engagement member portion and the fastening member portion show in in FIG. 3c.

FIG. 3d shows a side cross-sectional view of the engagement member portion 112 and the fastening member portion 114 shown in in FIG. 3c. As derivable from FIG. 3d, the centers of the openings 24b lie on an axis that coincides with an axis of the implant 100 and the elongated member 120 in a straight, unwound state thereof.

The engagement feature 142 is distanced from a plane defined by the bone-contacting bottom 134, such that it is configured to resiliently move towards the bone-contacting bottom 134 without reaching it, in order to ensure its functionality when the implant 100 is being wound around bone parts that are to be fixed and the elongated member 120 passing through the passage 154 pushes with its engagement features 126 the engagement feature 142 of the engagement member portion 112 in a direction towards the bone-contacting bottom 134. For this purpose, the maximum resilient displacement of the engagement feature 142 caused by the engagement features 126 of the engagement features portion 112 stops before reaching or at reaching a plane defined by the bone-contacting bottom 134 of the engagement member 112. This particular measure helps further reduce the height of the implant 100 in the top to bottom direction, which reduces the space required by the implant 100 in a human body and further helps avoid twisting of the implant 100 during insertion into the human body.

In order to reduce the height of the implant 10, 100 in a top 32, 132 to bottom 34, 134 direction, various combinations of features taken alone from the two embodiments described above are advantageous.

For example, the shoulders 44 from the first embodiment shown in FIG. 2 may be provided in a combination with the lateral step(s) 40 in the engagement features portion 116.

In a further example, a top surface of the separate pieces 24a in a bottom to top direction of the implant 10, 100 may form the maximum extension of the implant 10, 100 in a bottom to top direction of the implant 10, 100, in a straight, unwound state of the implant 10, 100, and/or a bottom surface of the separate pieces 24a in a top to bottom direction of the implant 10, 100 may form the maximum extension of the implant 10, 100 in a top to bottom direction of the implant 10, 100, in a straight, unwound state of the implant 10, 100.

Of course, the provision of separate pieces 24a also helps reduce the height of the implant 10, 100 by allowing a more flexible inclination of the separate pieces 24a towards the tensile stress in the implant 10, 100, such that the pieces 24a can be made thinner compared to a one-piece fastening member 24 with several openings 24b. However, the above measures for reducing the height of the implant 10, 100 are also applicable for an implant with a fastening member portion 14, 114 comprising a one-piece fastening member 24 with several openings 24b instead of separate pieces 24a each comprising one opening 24b.

The invention claimed is:

1. An implant for bone fixation, comprising:
    an elongated member configured to be wound around bone parts that are to be fixed;
    an engagement member coupled to the elongated member and configured to engage a portion of the elongated member so as to secure the elongated member in a loop around the bone parts;
    a fastening member coupled to the elongated member and the engagement member,
    wherein the fastening member comprises at least two separate pieces coupled to one another each comprising at least one opening for receiving a bone fastener, and
    wherein the separate pieces are coupled to each other by a material having a lower material strength than a material from which the separate pieces are made such that the material having the lower material strength is easier to cut in order to detach the implant after implantation.

2. The implant of claim 1, wherein the separate pieces are substantially aligned with a longitudinal axis of the elongated member of the implant when the implant is in a straight, unwound state.

3. The implant of claim 1, wherein the separate pieces are plates made from a metallic material.

4. The implant of claim 1, wherein the material coupling the separated pieces to each other is a polymeric material.

5. The implant of claim 1, further comprising:
    at least one visual indicator in a region of lower material strength between the separate pieces.

6. The implant of claim 1, wherein the fastening member is coupled to at least one of the elongated member and the engagement member by injection molding.

7. The implant of claim 6, wherein the visual indicator is defined by a portion of the fastening member that remains exposed from injection molding.

8. The implant of claim 1, wherein the elongated member has a bone-contacting surface and at least one first side extending substantially perpendicular to the bone-contacting surface and comprising a plurality of engagement features along a longitudinal extent of the at least one first side, and wherein the engagement member comprises at least one complementary deflectable engagement feature configured to engage at least one of the plurality of engagement features.

9. The implant of claim 8, wherein the elongated member comprises a second side opposite to the first side, and wherein the engagement features of the elongated member are arranged on both sides of the elongated member.

10. The implant of claim 9, wherein the elongated member comprises a lateral step that defines the first side, and wherein the engagement features of the elongated member are arranged within the lateral step.

11. The implant of claim 10, wherein the engagement member comprises at least one shoulder engaging with the lateral step.

12. The implant of claim 11, wherein the shoulder and the at least one complementary deflectable engagement feature are offset in a longitudinal extension of the engagement member.

13. The implant of claim 11, wherein the shoulder is closer to the elongated member than the at least one complementary deflectable engagement feature.

14. The implant of claim 8, wherein a groove on a surface opposite the bone-contacting surface extends in a direction substantially perpendicular to a longitudinal axis of the elongated member of the implant.

15. The implant of claim 8, wherein a groove on a surface opposite the bone-contacting surface extends in a direction substantially perpendicular to a longitudinal axis of the elongated member of the implant between the engagement member and the fastening member and/or between the fastening member and the elongated member.

16. The implant of claim 1, wherein the engagement member and the fastening member are arranged within a common plane in a straight, unwound state of the implant.

17. The implant of claim 16, wherein the engagement member comprises at least one deflectable engagement feature that substantially lies within the common plane, and/or that is deflectable within a plane which is parallel or orthogonal to the bone-contacting surface of the implant in a straight, unwound state thereof.

18. An implant for bone fixation, comprising:
an elongated member configured to be wound around bone parts that are to be fixed;
an engagement member coupled to the elongated member and configured to engage a portion of the elongated member so as to secure the elongated member in a loop around the bone parts;
a fastening member coupled to the elongated member and the engagement member,
wherein the fastening member comprises at least two separate pieces coupled to one another each comprising at least one opening for receiving a bone fastener,
wherein the elongated member comprises a lateral step and engagement features of the elongated member are arranged along a sidewall defined by the lateral step, and
wherein the engagement member comprises at least one shoulder engaging the lateral step.

19. The implant of claim 18, wherein the separate pieces are substantially aligned with a longitudinal axis of the elongated member of the implant when the implant is in a straight, unwound state.

20. The implant of claim 18, wherein the elongated member has a bone-contacting surface and at least one first side extending substantially perpendicular to the bone-contacting surface and comprising a plurality of engagement features along a longitudinal extent of the at least one first side, and wherein the engagement member comprises at least one complementary deflectable engagement feature configured to engage at least one of the plurality of engagement features.

* * * * *